United States Patent [19]

Schiestl

[11] Patent Number: 5,273,880
[45] Date of Patent: * Dec. 28, 1993

[54] PROCESS FOR DETECTING POTENTIAL CARCINOGENS

[75] Inventor: Robert H. Schiestl, Carrboro, N.C.

[73] Assignee: GeneBioMed, Inc., Rochester, N.Y.

[*] Notice: The portion of the term of this patent subsequent to Mar. 5, 2008 has been disclaimed.

[21] Appl. No.: 634,008

[22] Filed: Dec. 26, 1990

Related U.S. Application Data

[63] Continuation-in-part of Ser. No. 193,345, May 12, 1988, Pat. No. 4,997,757, which is a continuation-in-part of Ser. No. 137,325, Dec. 23, 1987, abandoned.

[51] Int. Cl.$^5$ .................... C12N 15/00; C12N 15/16; C12Q 1/68
[52] U.S. Cl. .................... 435/6; 435/172.1; 435/172.3; 435/240.2; 935/79
[58] Field of Search .................... 435/172.3, 172.1, 6, 435/240.2; 935/76, 78, 79

[56] References Cited

PUBLICATIONS

Fasullo et al. PNAS 84: 6215 (1987).
Irr et al. Banburg Report, No. 2, 504 (1979) Cold Spring Harbor, Abstract only.

Primary Examiner—Richard A. Schwartz
Assistant Examiner—J. L. Leguyader
Attorney, Agent, or Firm—Howard J. Greenwald

[57] ABSTRACT

There is disclosed a process for screening an agent to determine whether it increases the frequency of genome rearrangement in living matter.

In the first step of this process, there is provided viable mammalian cells which comprise repeated genetic elements in their haploid genome. These repeated genetic elements are selected from the group consisting of functional and non-functional genetic elements; and these elements are sufficiently homologous so that, under ambient conditions, they recombine with each other and give rise to an identifiable genome rearrangement.

In the second step of this process, the viable mammalian cells are exposed to the agent to be tested. Thereafter, they are incubated in growth medium which, after the exposed cells grow in it, facilitates the identification of those cells which have undergone said genome rearrangement.

In the last step of the process, the extent to which the exposed mammalian cells have undergone genome rearrangement is determined.

Also disclosed is the viable mammalian celline used in said process, the plasmid used to construct said celline, and a process for constructing said celline.

19 Claims, 3 Drawing Sheets

PROCESS FOR DETECTING POTENTIAL CARCINOGENS

CROSS-REFERENCE TO RELATED APPLICATIONS

This is a continuation-in-part application of applicant's copending patent application Ser. No. 07/193,345, filed on May 12, 1988, now U.S. Pat. No. 4,997,757, which in turn was a continuation-in-part of copending patent application Ser. No. 137,325, filed on Dec. 23, 1987, now abandoned.

FIELD OF THE INVENTION

A process for predicting the carcinogenic potential of a compound or composition using mammalian cells wherein the cells are incubated in the presence of the compound or composition.

BACKGROUND OF THE INVENTION

About 700,000 new cases of cancer affect North Americans each year. It is estimated that from about 70 to about 90 percent of these new cancer cases are linked to environmental carcinogens. Epidemiologists estimate that at least about 70 percent of human cancer would be preventable if the main risk and antirisk factors could be identified. One epidemiological example of this phenomenon is colon and breast cancer. These are among the major types of cancer, but they are quite rare among Japanese living in Japan. However, Japanese living in the United States have a relatively high incidence of this disease.

There are in excess of about 80,000 chemicals in commercial production. Over 400,000 new organic compounds are synthesized every year, and at least 1,000 of them each year will eventually be introduced into economic use. There is a need to be able to determine which of these new compounds will cause cancer. However, it is difficult to predict without testing whether any particular chemical will cause cancer.

The most reliable means for determining whether a particular compound is carcinogenic is a long term assay, which generally is based on the experimental assessment of the potential of the substance to induce tumors in rodents. Long term assays usually take from 6 to 12 months to conduct, and they are relatively expensive. Because of the time and/or the expense involved, it is not feasible to conduct long term assays in many situations, especially where one is seeking a preliminary indication as to whether to proceed with the development of a particular substance.

The need for relatively fast and inexpensive means for preliminarily evaluating the cancer-causing potential of new chemicals has led to the development of many short term assays; some of these short term assays are described in column 4 (lines 13–44) of U.S. Pat. No. 4,701,406, the disclosure of which is hereby incorporated by reference into this specification. The most widely known of these short-term assays is the Ames Assay. This Assay is based upon the assumption that carcinogens will cause the genetic reversion of certain mutant strains of the bacteria *Salmonella typhimurium*. In other words, the mutant strains revert to their normal form in the presence of mutagens. A description of the Ames Assay may be found, e.g., in an article by Ames et al., "Methods for Detecting Carcinogens and Mutagens with the Salmonella/Mammalian-Microsome Mutagenicity Test," *Mutation Research*, vol. 31 (1975), pp. 347–364.

One disadvantage of the Ames Assay is that many classes of carcinogenic compounds consistently show poor responses in this assay. Thus, as is disclosed at column 4 of U.S. Pat. No. 4,701,406, the Ames Assay is not very useful for evaluating certain metals, steroid hormones, and chlorinated hydrocarbons which, although they are known to be carcinogens, give very poor responses.

One of the major problems with the Ames Assay is that, although it is useful for evaluating certain mutagenic compounds, it is not generally useful for evaluating carcinogenic compounds which are not mutagenic. See, for example, McCann et al., "Detection of Carcinogens as Mutagens in the Salmonella/Microsome Test: Assay of 300 Chemicals, *Proc. Nat. Acad. Sci. USA*, vol. 72, No. 129 (1975), pp. 5135–5139. Also see McCann et al., "Detection of Carcinogens as Mutagens in the Salmonella/Microsome Test: Assay of 300 Chemicals Discussion, "*Proc. Nat. Acad. Sci. USA*, vol. 73, No. 3 (1976), pp 950–954.

Short term tests involving mutation and recombination assays with the yeast *Saccharomyces cerevisiae* have been developed. However, these yeast assays are only able to detect about 74 percent of the known carcinogens as being positive. See, for example, an article by Zimmermann et al. appearing in Mutation Research, vol. 133 at pages 199–244 (1984).

The prior art teaches the use of both the Ames Assay and the aforementioned yeast assay in combination, but even the use of both of these assays fails to detect many nonmutagenic carcinogens. See, e.g., the aforementioned article by Zimmermann et al.

The prior art also teaches the use of other in vitro mammalian assays, see e.g. a book by Milman et al. entitled "Handbook of carcinogen testing", Noyes Publications, New Jersey, the publication of which is incorporated by reference into this specification. The mammalian assays also fail to detect many nonmutagenic carcinogens. The following examples are taken from the aforementioned reference. Thus for example the tests for sister chromatid exchange as well as for chromosome aberrations with mammalian cells are both negative for ethionene, ethylenethiourea and safrole. Thus, for example, the syrian hamster embryo clonal transformation procedure is negative with aniline. Thus, for example the rat liver foci assay is negative with safrole and thioacetamide.

Not only do the prior art short-term tests fail to show positive results with many known carcinogens, but they also usually fail to indicate whether a prospective carcinogen will cause genome rearrangement. There is a substantial body of literature indicating that compounds which cause genome rearrangement might cause cancer. Thus, it has been shown that the excision of retroviruses from genomes can cause cancer; see Bishop, Ann. Rev. Biochem. 52:301-354 (1983) and Bishop, Cell 42:23-38 (1985). Thus, it has been shown that amplification of specific human DNA sequences up to 120 times are associated with cancer, see Montgomery et al., Proc. Natl. Acad. Sci. USA 80:5724-5728 (1983) and Schwab et al., Proc. Natl. Acad. Sci. USA 81:4940-4944). Thus, it has been shown that immunoglobulin class switching in B lymphocyte differentiation is associated with cancer; see Brown et al., Proc. Natl. Acad. Sci. USA 82:556-560 (1985), Korsmeyer et al., Proc. Natl. Acad. Sci. USA 80:4522-4526 (1983), and Cleary et al., Proc. Natl. Acad. Sci. USA 81:593-597 (1984). Thus it has also been shown that rearrangements involving the T Cell receptor gene are associated with cancer; see Flug, Proc. Natl. Acad. Sci. USA 82:3460-3464 (1985) and Minden et al. Proc. Natl. Acad. Sci. USA 82:1224-1227 (1985). Thus, it has also been shown that amplification preceded by mutation of a gene is associated with cancer; see, e.g., Fujita, Proc. Natl. Acad. Sci. USA 82:3849-3853 (1985). Thus, it has also been shown that deletions in recessive oncogenes are associated with carcinogenesis such as retinoblastoma; see, e.g., Hansen and Cavanee, Cell 53:172-173 (1988), see also, Ponder, Nature 335:400-402 (1988). The role of genome rearrangement in carcinogenesis has also been discussed in more general terms in Klein, Nature 294:313-318 (1981), Pall, Proc. Natl. Acad. Sci. USA 78:2465-2468 (1981), Cairns, Nature 289:353-357 (1981), and Wintersberger, Naturwissenschaften 69:107-113 (1982).

It is an object of this invention to provide a short-term assay system which can be used to evaluate many bactericidal and antibiotic compounds.

It is another object of this invention to provide a short-term assay which can be used to evaluate many non-mutagenic compounds which are carcinogenic and which do not show positive results in the prior art Ames Assay, yeast assays and mammalian cell culture systems.

It is yet another object of this invention to provide a short-term assay system which can be used to evaluate many compounds or compositions which cause genome rearrangement.

SUMMARY OF THE INVENTION

In accordance with this invention, there is provided a process for screening an agent in order to determine whether such agent increases the frequency of genome rearrangement in living matter.

In the first step of this process, there is provided viable mammalian cells which comprises repeated genetic elements in their haploid genome. These repeated genetic elements are selected from the group consisting of functional and non-functional genetic elements; and these elements are sufficiently homologous so that, under ambient conditions, they recombine with each other and give rise to an identifiable genome rearrangement.

In the second step of this process, the viable mammalian cells are exposed to the agent to be tested. Thereafter, they are incubated in growth medium which, after the exposed cells grow in it, facilitates the identification of those cells which have undergone said genome rearrangement.

In the last step of the process, the extent to which the exposed mammalian cells have undergone genome rearrangement is determined.

Also disclosed is the viable mammalian celline used in said process, the plasmid used to construct said celline, and a process for constructing said celline.

DESCRIPTION OF THE DRAWINGS

The present invention will be more fully understood by reference to the following detailed description thereof, when read in conjuction with the attached drawings, wherein like reference numerals refer to like elements, and wherein:

FIG. 3 is a schematic of the constituents of another preferred embodiment showing recombination between the repeated elements giving rise to a genome rearrangement which is a gene duplication and reconstitution of a selectable gene from different parts of it is selected for;

FIG. 4 is a schematic of the constituents of yet another preferred embodiment showing recombination between the repeated elements giving rise to a genome rearrangement which is a translocation and reconstitution of a selectable gene from different parts of it on different chromosomes is selectable for;

FIG. 5 is a schematic of the constituents of yet another preferred embodiment showing recombination between the repeated elements giving rise to a genome rearrangement which is a deletion and the reversion of a disrupted gene is selectable for.

DESCRIPTION OF THE PREFERRED EMBODIMENTS

Figure 1:
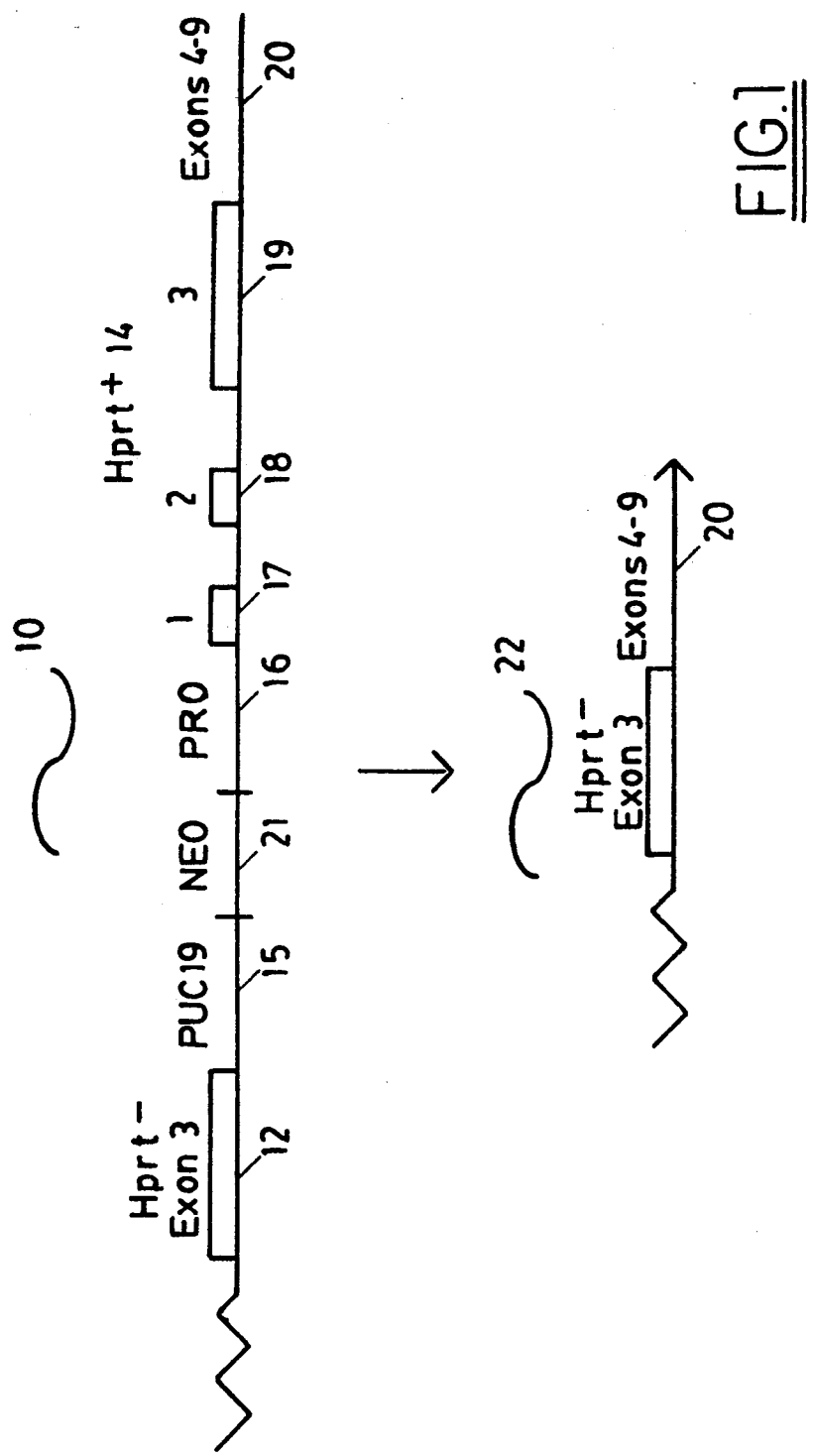
FIG. 1 is a schematic of the constituents of a preferred embodiment showing recombination between the repeated elements giving rise to a genome rearrangement which is a deletion and the presence of the gene to be fully or partly deleted by said genome rearrangement is selected against.

The present invention provides a short term assay for identifying potential carcinogens. This system screens for a genetic endpoint, namely genome rearrangement, which is frequently associated with cancer.

As used in this specification, the term genetic endpoint refers to the secondary effect of genotoxic substances. Genotoxic substances interact with DNA and thereby change its structure. These substances either can bind to the DNA, can modify one or more bases in the DNA strands, can form adducts with one or more of the bases, can alkylate the DNA, can induce single or double strand breaks, can induce bases adjacent to each other on one DNA strand to pair with each other instead of with the complementary bases on the opposite DNA strand, can intercalate between the stacked bases of the DNA double helix, can cause the DNA strands to bind to each other by other than hydrogen bonds, and the like. These adverse interactions, which are often referred to as lesions, are discussed in U. Goodenough's "Genetics," Third Edition (Saunders College Publishing, New York, 1984), the disclosure of which is hereby incorporated by reference into this specification.

DNA repair enzymes recognize the damage caused by genotoxic substances or by other causes (such as spontaneous damage or misreplication) and repair such damage. In the process of repairing the damage, the native DNA sequence of bases is changed. Wherever a change in the DNA sequence has been caused by both the damage and the subsequent repair, a genetic endpoint exists.

By way of illustration and not limitation, a mutation is a genetic endpoint. As used in this specification, the term mutation refers to a change in a single base pair or in several base pairs. Thus, for example, if one of the bases in a base pair is changed, a lesion occurs, but this is not a mutation within the meaning of this specification; only when both of the complementary base pairs change does a mutation occur. The term mutation, as used in this specification, is equivalent to the term "point mutation" as that term is defined on page 202 of the aforementioned Goodenough book.

The base pair may be changed by several mechanisms. One base pair may be changed to another one. Certain chemicals change the chemical identity of one of the bases, the DNA repair or replication enzymes might misread the damaged base, and the enzymes then might modify the heretofore unchanged base.

By way of illustration and not limitation, crossing over is a genetic endpoint. Crossing over is reciprocal recombination joining different homologous DNA molecules so that genes combined as A-B and a-b are now arranged A-b and a-B. Crossing over might result from the breaking and reunion between two homologous chromosomes. Homologs are chromosomes that are sufficiently similar to pair during meiosis.

By way of illustration and not limitation, gene conversion is a genetic endpoint. As used in this specification, gene conversion is the nonreciprocal transfer of information in terms of DNA sequence from one DNA double strand to another so that, for example, genes ABC and abc are converted to AbC and abc. Gene conversion is discussed on pages 561-565 of the aforementioned Goodenough book.

By way of illustration and not limitation, recombination is a genetic endpoint. Recombination includes both crossing over and gene conversion. Homology between the recombining alleles usually has to exist before recombination occurs.

Genome rearrangement is another genetic endpoint, the one for which the system of this invention tests. A genome is a complete haploid set of chromosomes. A haploid organism is a viable structure having a single set of chromosomes; by comparison, a diploid organism has two sets of chromosomes. A genome rearrangement is any genetic event which rearranges the order of genes in a haploid genome, thereby creating a new environment for particular genes either on a different chromosome or on the same chromosome in a different position. Genome rearrangements include, e.g., deletions, translocations, gene amplification, and rearrangements within genes.

Deletions identify a loss of any DNA sequence from the genome. A translocation involves the interchange of the position of sequences on nonhomologous chromosomes. Gene amplification is a multiplication of a DNA sequence whereby, e.g., a gene sequence is duplicated, triplicated, etc. Intrachromosomal recombination is recombination within one chromosome, either intrachromatid (within one chromatid) or between sister chromatids. As is known by those skilled in the art, the term chromatid refers to one of the two parts of a chromosome which exist after replication, there being one DNA double helix before replication, and two identical DNA double helices after replication, the basis elements of the two chromatids, attached at the centromere of a replicated chromosome; intrachromosomal recombination often causes a genetic endpoint. Interchromosomal recombination is recombination between homologous chromosomes in a diploid cell, and it also often causes a genetic endpoint.

Chapters 7, 17, and 19 of the aforementioned Goodenough book discuss genetic endpoints. Many of the terms used in this specification are defined in the Goodenough book and also in a text by W. Ralph SIngleton entitled "Elementary Genetics", Second Edition (American Book Company, New York, 1962), at pages 537-559, the disclosure of which is hereby incorporated by reference into this specification.

In the process of this invention, mammalian cells with certain specified properties could be used in conjunction with a specified medium to test for the presence of chemicals causing a genome rearrangement. The mammalian cells in this process must undergo recombination between repeated genetic elements and thereby cause genome rearrangement which must be selectable for or otherwise identifiable.

Recently it has been made feasible to culture mammalian cells outside the mammalian body and this technique is now being used in many laboratories. For more basic information about the mammalian cell culture technology see "Animal cell culture: A practical approach" by R. I. Frishney, IRL Press, Washington, D.C. and "Molecular genetics of mammalian cells" in Methods in Enzymology, Vol. 151 by M. M. Gottesman, Academic Press, New York, the disclosure of both books is hereby incorporated by reference into this specification.

Several different sources of mammalian cells can be used in this process such as human, monkey, mouse, rat or hamster cells. For a characterization of useful cell lines see pages 3 to 84 of the aforementioned book "Molecular genetics of mammalian cells" by Gottesman. Not every mammalian cell line works in the process of this invention. The process utilizes those viable mammalian cells which contain repeated genetic elements (alleles) in their haploid genome.

The term "viable", as used in connection with alleles, refers to the presence of at least two homologous elements in the haploid genome. Thus, by way of illustration, mammalian chromosomes normally only contain one Hprt gene coding for the hypoxanthine-guanine phosphoribosyltransferase. In order to be used in the process of this invention, the mammalian chromosomes should contain at least one part of the HPRT (or other) genes duplicated in the haploid genome.

By way of illustration and not limitation, one of the classes of homologous elements, which can be used, is the two alleles of one gene. The alleles may be either functional or nonfunctional. When nonfunctional alleles are used, they may interact by recombination with each other, thereby giving rise to at least one functional allele which can be selected for. When two functional or nonfunctional alleles are used, they may also interact by recombination with each other; by way of illustration, two functional or nonfunctional alleles may recombine with each other to delete the region between the two alleles which can be selected against. In either case, the homologous alleles recombine to create a genome rearrangement. It should also be noted that, regardless of which homologous elements are used, they must recombine to give rise to a genome rearrangement.

Thus, by way of illustration, one class of homologous elements which can be used includes at least two alleles, at least one of which is nonfunctional, and/or at least one of which is functional.

FIG. 1 illustrates one class of homologous elements which can be present in the mammalian cells used in applicant's process. Referring to FIG. 1, construct 10 is comprised of Hprt- allele 12, the homologous Hprt- allele 14. A normal HPRT gene consists of a promoter and exons 1 to 9. The Hprt allele 12 is nonfunctional (Hprt-) and consists only of exon 3 of the Hprt gene. The HPRT allele 14 is functional (HPRT+) and consists of a promoter (16) and exons 1 (17), exon 2 (18)

exon 3 (19) and exons 4 to 9 (20). Between Hprt alleles 12 and 14 sequences of the vector PUC19 (15) and the NEO gene (21) are present. Both the PUC19 vector and the NEO gene may not be essential for this process and may be ommitted or replaced without any adverse effect.

The construct of FIG. 1 is only one of many within the scope of this invention which can utilize at least two alleles. Thus, by way of illustration and not limitation, alleles 12 and 14 may be the thymidinekinase gene Tk and the like.

In the construct of FIG. 1, a mutation may be present. As used in this specification, the mutation causes the celline to gain sensitivities or resistance to the selection medium which changes the resistance of the wild type. Thus, referring to FIG. 1, construct 10 contains a functional and a nonfunctional Hprt gene so that the celline growth in the presence of hypoxanthine, aminopterine and thymidine. When the system used in applicant's invention is constructed, gene 14 is selected for to give rise to construct 10. In this process, a spontaneous deletion is corrected. By way of illustration, as shown in FIG. 1, the Hprt gene is corrected. This selection process will be illustrated later in this specification and can be carried out with any other gene which can be selected against such as Tk or the like.

Construct 10 spontaneously reverts to its mutant form 22 under ambient conditions. Thus, for example, a construct which is identical to construct 10, reverts to the Hprt- gene 22 at a frequency of about $8 \times 10^{-7}$ occurrences per cell. The only difference to construct 10 is that the published construct lacks the NEO gene 21, which may or may not change the frequency of recombination. This celline, lacking the NEO gene 21, has been designated "E14TG2a with pNMR133" and has been constructed by Doetschman et al. and published in Nature (1987) volume 320 pages 576 to 578. Another celline also lacking the NEO gene and being similar to pNMR133 has been published in an article by Thompson et al. 1989 in Cell, vol. 56 on pages 313–321. Both of those constructs are readily available to those skilled in the art. These publications are hereby incorporated by reference into this specification. It is predicted that one of the unique advantages of construct 10 may be that, when the celline containing construct 10 is growing in the presence of a nonmutagenic carcinogen, the rate of reversion to mutant gene 22 is expected to increase substantially.

As those skilled in the art are aware, one can measure the rate of reversion of HPRT+ to Hprt-by means well known to those skilled in the art. Thus, for example, one can plate certain numbers of cells on a medium containing 6-thioguanine (6-TG). This and other mammalian genetics methods are described in detail in the aforementioned publication by M. M. Gottesman and the one by R. I. Frishney.

In one of the preferred embodiments of this invention, illustrated in FIG. 1, the viable mammalian cells contain repeated genetic elements which recombine to give rise to an identifiable deletion at a rate of at least about $1 \times 10^{-11}$ occurrences per cell per generation, as measured in accordance with the procedure described in the above references.

As used in this specification, the term "identifiable" refers to a rearrangement which, when the cells in which it is present are growing in a suitable selection medium, cause the cells to exhibit some phenotype which is different from that of cells which have not undergone rearrangement. Thus, by way of illustration, if the genome rearrangement causes the cells to form countable and/or visible colonies, the rearrangement is identifiable if cells which have not undergone the rearrangement do not form countable and/or visible colonies in the selection medium, or if the cells which have not undergone said rearrangement form colonies which are distinguishable in any means from the colonies formed by the cells which have undergone said rearrangement. Thus, by way of illustration, if the genome rearrangement causes the cells to form colonies identifiable by different color from the colonies which have not undergone the rearrangement, the rearrangement is identifiable. Thus, by way of illustration and not limitation, if the genome rearrangement causes the cells to grow, the growth of these cells in selection medium may be measured (if adapted to mammalian cells) by techniques similar to the ones described in U.S. Pat. No. 4,256,832 of Findl et al. (which technique detects oxygen consumption of growing cultures), and this growth is thus identifiable. Thus, by way of illustration and not limitation, one adaptation to mammalian cells may be measuring the acidification of the medium by color change or other changes instead of measuring the oxygen consumption.

Referring again to FIG. 1, if construct 10, in the presence of the medium to be discussed later on, reverts to gene 22 in the presence of a chemical at a rate substantially higher than $5 \times 10^{-7}$ occurrences per cell per generation, then the chemical induces the recombination mechanism tested for.

Figure 2:
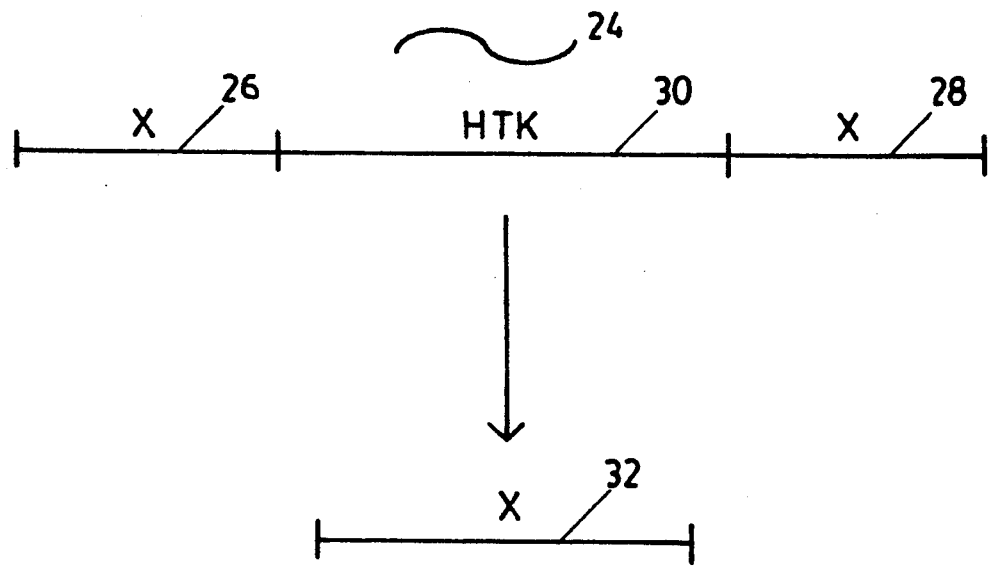
FIG. 2 is a schematic of the constituents of a preferred embodiment showing recombination between the repeated elements giving rise to a genome rearrangement which is a deletion and the presence of the gene to be deleted by said genome rearrangement is selected against.

In the embodiment illustrated in FIG. 2, a construct 24 which contains two homologous genetic elements 26 and 28 is shown. Genetic elements 26 and 28 can be— but need not be—alleles or genes; any genetic elements which have sufficient homology with each other to recombine can be used as elements 26 and 28. Thus, by way of illustration and not limitation, one can use any of the aforementioned genes, any DNA sequence which has enough homology to recombine, any cloned gene and the like.

Referring again to FIG. 2, the recombination occurs and deletes the allele 30. Allele 30 must be capable of being selected against so that elements 26 and 28 can recombine to form structure 32 which contains only one copy of the combination of elements 26 and 28 which contains all or part of the genetic information of element 26 and/or all or part of the genetic information of element 28.

By way of illustration, allele 30 can be the HTK gene. When this HTK gene is present in construct 24, the celline containing this construct is unable to grow in a medium containing hypoxanthine and bromodeoxyuridine (HBu medium). Under ambient conditions, alleles 26 and 28 recombine with each other to form a deletion of the HTK+ gene, thereby producing allele 32. After recombination, however, the strain containing allele 32 is able to grow in or on Hbu medium. In the embodiment of this Figure, the deletion of one sequence is selected for. The recombination occurs at a specified rate, which can be determined by methods to be discussed later on in this specification.

Other wild type allele 30's can also be used. Thus, for example, instead of the HTK gene, one can also use HPRT and the like. When, for example, a celline containing the HPRT allele as allele 30 in construct 24, then the strain is unable to grow in a medium containing 6-thioguanine. As before, the alleles 26 and 28 recombine with each other to produce allele 32, and the celline containing allele 32 is able to grow in the presence of 6-thioguanine.

With regard to the embodiment of FIG. 2, applicant has discussed the TK, and HPRT alleles 30. However, as those skilled in the art are aware, other genes can be used as long as they can be selected against with the use of a specified medium. These other genes and media are within the scope of this invention.

Figure 3:
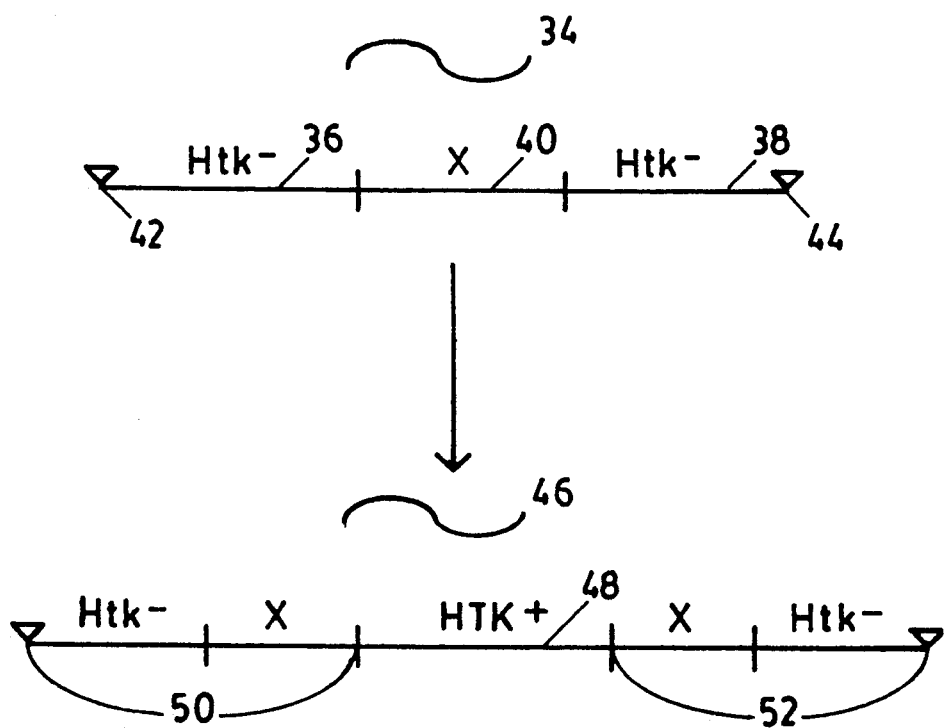

In the embodiment illustrated in FIG. 3, a construct 34 is illustrated which is comprised of two nonfunctional alleles, 36 and 38 and spacer DNA 40. As used in this specification, the term spacer DNA refers to any sequence of DNA which serves as a spacer between two repeated homologous elements. Points 42 and 44 indicate where deletions are present in the nonfunctional alleles. Thus, referring to the particular embodiment illustrated in FIG. 3, construct 34 is comprised of Htk-36, the homologous Htk-38, and the spacer DNA 40; points 42 and 44 indicate where deletions have occurred or have been constructed from the parent Htk+ gene.

The construct of FIG. 3 is only one of many within the scope of this invention which can utilize at least two nonfunctional alleles. Thus, by way of illustration and not limitation, alleles 36 and 38 may be Hprt-, neo-, hph-, Xgpt-, hyg- and the like. Thus, by way of illustration and not limitation, the spacer DNA 40 may be any DNA sequence but it is not essential for the system and thus it might be omitted without adverse affects.

In the construct of FIG. 3, a selectable gene must be present. Thus, referring to FIG. 3, construct 34 contains two nonfunctional Htk- alleles so that the celline is unable to grow in the presence of hypoxanthine, aminopterine and thymidine (HAT medium). If one were to substitute Hprt- for the Htk- allele, the celline would also be unable to grow on HAT medium. If one were to substitute neo- (coding for neomycin resistance in bacteria) for the Htk- allele, the celline would be unable to grow on medium containing G418. If one were to substitute hph- or the hyg- gene (coding for hygromycin B phosphotransferase) for the Htk- allele, the celline would be unable to grow on medium containing hygromycin B. If one were to substitute Xgpt- (coding for bacterial xanthine guanine phosphotransferase) for the Htk- allele, the celline would be unable to grow on medium containing guanine and mycophenolic acid.

Construct 34 spontaneously undergoes genome rearrangement under ambient conditions to produce construct 46. It should be noted that this rearrangement involves the unequal pairing of the Htk- alleles, each one residing on one sister chromatid after DNA replication. After pairing, these alleles recombine with each other to yield construct 46. The rearrangement occurs at a certain rate under ambient conditions, but the rate of the rearrangement is expected to be increased if the cell would grow in the presence of many DNA damaging agents.

Construct 34 is unable to grow in the presence of the aforementioned substances. The genome rearrangement which is expected to be favored by the presence of the DNA-damaging agents forms construct 46 which is able to grow in the presence of the aforementioned substances or whatever alleles 36 and 38 are unable to grow in the presence of.

Unlike the constructs produced in FIGS. 1 and 2, the arrangement of alleles in construct 46, after the genome rearrangement, is comprised of the HTK allele 48 flanked by a duplication 50 and 52 of a portion of construct 34. It is believed that the rearrangement which occurs in this case involves unequal sister chromatid exchange or unequal sister chromatid conversion.

Figure 4:
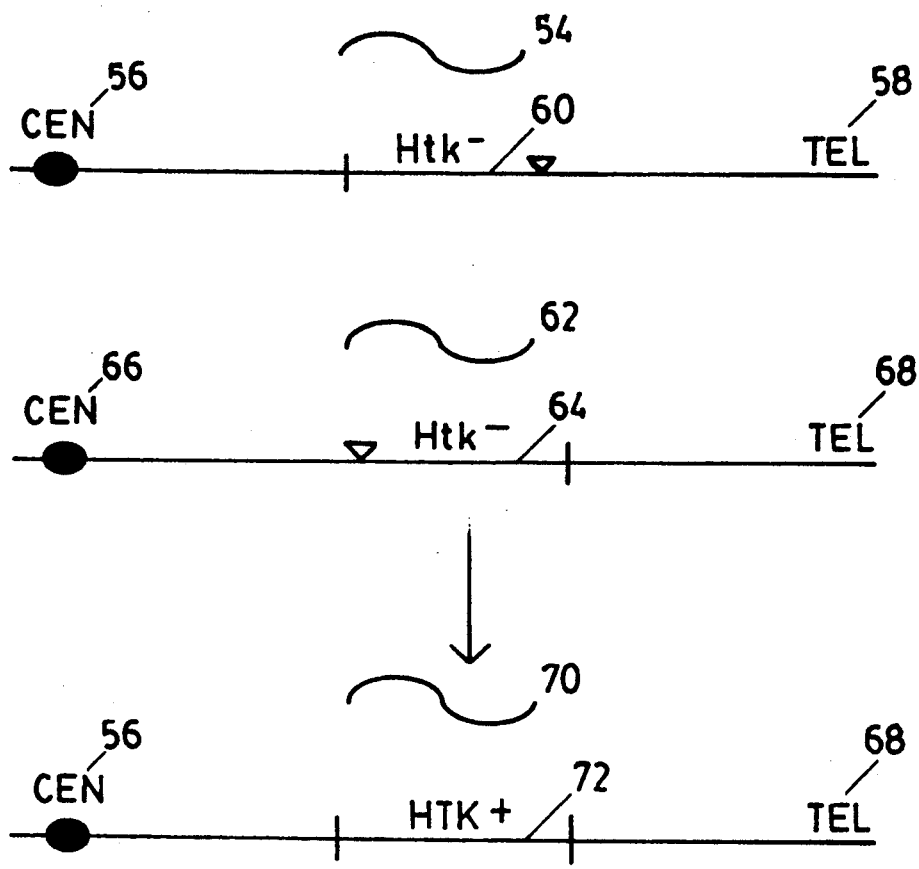

FIG. 4 illustrates yet another embodiment involving two homologous alleles which, unlike the constructs of FIGS. 1, 2, and 3, each reside on different, non-homologous chromosomes. Referring to FIG. 4, chromosome 54 is comprised of centromere 56 and telomere 58. As those in the art are aware, the term centromere refers to the spindle fiber attachment region of a chromosome. The term telomere refers to the region forming each end of the chromosome.

Referring again to FIG. 4, chromosome 54 is comprised of Htk- allele 60. Non-homologous chromosome 62 is comprised of Htk- allele 64, centromere 66, and telomere 68. The chromosomes 54 and 62 are non-homologous; the alleles 60 and 64 are homologous and undergo recombination to give rise to the wild type HTK allele 72 on the hybrid chromosome 70, which comprises centromere 56 from chromosome 54 and telomere 68 from chromosome 62. This mechanism is known to those skilled in the art as translocation.

As is the case with the constructs of FIG. 3, one can use other alleles of genes Hprt, neo, hph (hyg), Xgpt, and the like. Any nonhomologous chromosome pair can be used to provide chromosomes 54 and 62.

The medium used in any particular situation wherein the construct of FIG. 4 will be used in the process should be the respective medium selecting against the alleles used. If, e.g., alleles 60 and 64 are Htk-, then a selection medium should contain hypoxanthine, aminopterine and thymidine. If, e.g., alleles 60 and 64 are neo-, then the selection medium should contain G418, etc.

Cells containing the constructs 54 and 62 are unable to grow in the presence of the respective factor(s). However, cells containing the construct 70 formed by the rearrangement are able to grow in the presence of the respective factor(s).

Figure 5:
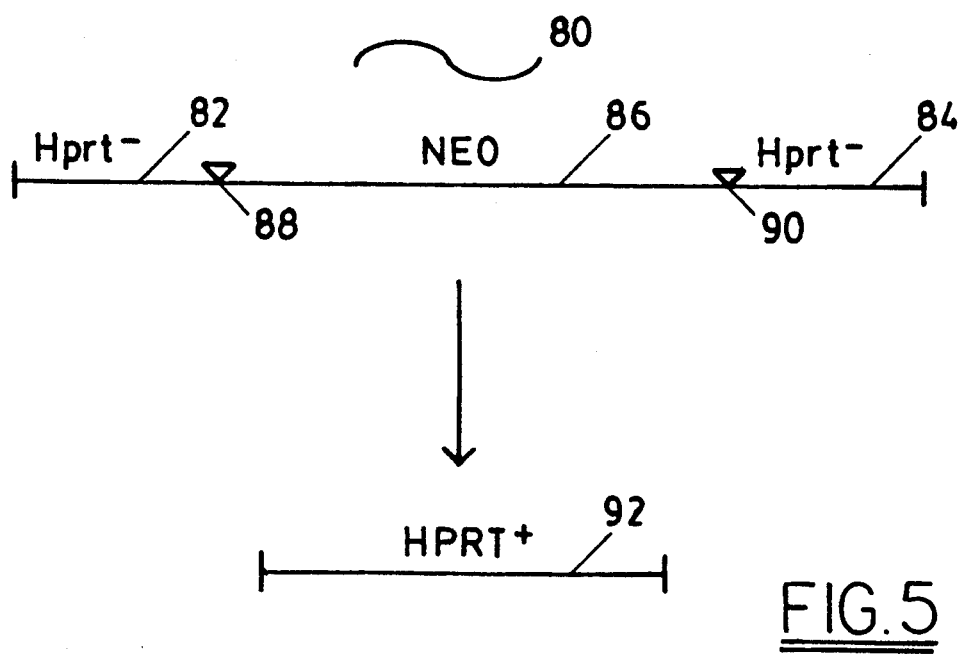

FIG. 5 illustrates one class of homologous elements which can be present in the mammalian cells used in applicant's process. Referring to FIG. 5, construct 80 is comprised of Hprt- allele 82, the homologous Hprt- allele 84, and the NEO gene 86. Points 88 and 90 indicate where deletions have been constructed in vitro from the parent HPRT gene. Because of the deletions constructed at points 88 and 90, alleles 82 and 84 are non-functional; however, when they recombine, they form the functional HPRT+ gene The construct of FIG. 5 is only one of many within the scope of this invention which can utilize at least two nonfunctional alleles. Thus, by way of illustration and not limitation, alleles 82 and 84 may be tk-, neo-, hph- (hyg-), Xgpt-, and the like. Thus, by way of illustration and not limitation, the NEO gene 86 may be replaced by HPRT, TK, HPH (HYG), XGPT, and the like.

In the construct of FIG. 5, mutant alleles must be present. As used in this specification, a mutant allele is a mutation which causes the celline to be sensitive to certain factor(s) to which the same celline with a wild type allele would be resistant. Thus, referring to FIG. 5, construct 80 contains two nonfunctional Hprt- alleles which cause the celline to be unable to grow in the presence of hypoxanthine, aminopterine and thymidine. If one were to substitute neo- for the Hprt- allele, the celline would be unable to grow in the presence of G418.

Referring again to FIG. 5, gene 86 should be a wild type allele, i.e., when the system used in applicant's invention is constructed, gene 86 is selected for to give rise to construct 80. In this process, a wild type allele is disrupted. By way of illustration, as shown in FIG. 5, the HPRT gene is disrupted. This selection process will be illustrated later in this specification and can be carried out with any other selectable wild type gene such as TK and the like.

The construction of construct 80 and a celline harboring that construct has been published by Thomas and Capecchi in Cell (1987) volume 51 on pages 503-512 and is available to those skilled in the art.

Construct 80 should spontaneously revert to its respective wild type gene 92 under ambient conditions. Thus, for example, the celline containing construct 80 illustrated in FIG. 5 should revert to the HPRT+wild type gene 92 at an expected frequency of more than $1 \times 10^{-11}$ occurrences per cell. One of the unique expected advantages of construct 80 is that, when the celline containing construct 80 would be growing in the presence of a nonmutagenic carcinogen, the rate of reversion to its wild type gene 92 would increase substantially.

The most preferred class of constructs for use in applicant's process are those described in FIG. 1 and FIG. 5 and in that portion of the specification which corresponds to FIG. 1 and FIG. 5. In this portion of the specification, a detailed description will be given of how to construct one of the embodiments of construct 10, it being understood that this description is equally applicable to other embodiments of construct 10.

On page 577 of the publication by Doetschman et al. (1987), Nature vol. 330, the HPRT locus and the construction of a construct similar to construct 10 is shown. On page 314 of an article by Thompson et al. 1989 published in Cell, vol. 56 on pages 313-321 another construct similar to construct 10 is shown. The only important difference to construct 10 is that in the published constructs the NEO gene 21 is missing. Several restriction sites are shown on the respective pages of the aforementioned publications. As those in the art are aware, a restriction enzyme digests or cuts DNA at certain recognition sequences, i.e., certain sites in the DNA molecule where the base sequence is recognized by the enzyme. Some restriction enzymes and the sites they recognize on the DNA are described on pages 110-111 of the aforementioned Goodenough book.

The plasmid DWM101 which contains the first three exons of the Hprt gene has been published in the above mentioned paper by Thompson et al. More information about the Hprt gene can be obtained from the following references: A publication by Thomas et al. entitled "Site-directed mutagenesis by gene targeting in mouse embryo derived stem cells", published in Cell (1987) vol. 51 pages 503-512; in a publication by Caskey et al. entitled "The Hprt locus", published in Cell, vol. 16, pages 1-9 and in a publication by Thompson et al. published in Cell (1989) vol. 56 on pages 312-321 and in an article by Reid et al. (1990) published in Proc. Natl. Acad. Sci. USA (1990), vol. 87, pages 4299-4303. These articles which are hereby incorporated by reference into this specification.

As will be readily available to those skilled in the art, plasmids pWM101 described in the above mentioned article by Thompson et al. and pMC1Neo described in the above mentioned article by Thomas et al. were chosen by the applicant in order to construct the plasmid pRS179 used in this specification. When other constructs are desired, other plasmids can be used as starting materials. As is well known to those in the art, these other plasmids are readily available, and their construction is well known to those in the art.

In the process of producing one of the preferred embodiments used in the invention, plasmid pWM101 has been cut at the restriction sites for the endonuclease HindIII and both fragments subcloned. The resulting fragments have been isolated. The procedure for digesting plasmids with restriction enzymes and of isolating the fragments so digested is well known to those skilled in the art. Thus, by way of illustration and not limitation, one may refer to a publication by T. Maniatis et al. entitled "Molecular Cloning: A Laboratory Manual", (Cold Spring Harbor Laboratory, Cold Spring Harbor, N.Y., 1982). In the Maniatis Laboratory Manual, restriction enzymes are disclosed on pages 97-107, and the isolation of gene fragments by Gel Electrophoresis is described on pages 149-186. The Maniatis Laboratory Manual is hereby incorporated by reference in its entirety into this specification.

The restriction enzyme digest was electrophoresed on a agarose gel containing 0.7 percent agarose and TBE buffer containing 0.089 molar Tris base, 0.089 molar boric acid, and 0.01 molar disodium ethylene diamine tetra-acetate dihydrate (EDTA). This electrophoresis buffer is described on page 454 of the aforementioned Maniatis Laboratory Manual.

The electrophoresis was carried out with a current of 30 volts for about 8 hours, and the DNA fragments were stained with ethidium bromide; the ethidium bromide was used at a concentration of 0.5 micrograms per milliliter of buffer solution.

The fragments were visualized under ultra-violet light with a frequency of 300 nanometers. Isolation was then carried out in accordance with the procedure of Dretzten et al., "A reliable method for the recovery of DNA fragments from agarose and acrylamide gels", Anal. Biochem. 112: 295-298 (1981), the disclosure of which is hereby incorporated by reference into this specification. The procedure described by Dretzten is also mentioned on pages 168-169 of the aforementioned Maniatis Laboratory Manual. In this procedure, the DNA is collected by binding it to DEAE-cellulose paper and by elution from the paper.

The isolated fragments from plasmid pWM101 were ligated with DNA ligase purchased from the Bethesda Research Laboratory, of Gaithersburg, Md. The fragment containing the vector was ligated onto itself and the resulting plasmid was named W43, the fragment without a vector was ligated with pUC8 after digestion with HindIII and named W78. The ligation procedure is well known to those skilled in the art and is described, in, e.g., pages 286 to 307 of the aforementioned Maniatis Laboratory Manual. The particular ligation buffer used is described on page 474 of the Maniatis Laboratory Manual. This buffer contained 0.66 moles of Tris base buffered to a pH of 7.5 with hydrochloric acid, 50 millimolar of magnesium chloride, 50 millimolar of dithiothreitol, and 10 millimolar of adenosine triphosphate.

With this ligation, the E. coli strain SF8 was transformed, and ampicillin-resistant colonies containing the plasmid pRS179 were isolated. It is believed that strain SF8 has the following genotype: hsdr-, hsdm-, recA1, supE44, lacz4, leuB6, proA2, and thi1. The structure of the plasmid pRS179 was verified by restriction analysis (see, e.g., pages 363-402 of the Maniatis Laboratory Manual).

Plasmid W78 was digested with EcoRI upstrem of the first exon of the Hprt gene. Using XhoI linkers a XhoI site has been introduced flanked by EcoRI site. The creation of new restriction sites with linkers is well known to those skilled in the art. Thus, by way of illustration and not limitation, one may refer to the above cited publication by T. Maniatis et al. entitled "Molecular Cloning: A Laboratory Manual", (Cold Spring Harbor Laboratory, Cold Spring Harbor, N.Y., 1982). The resulting plasmid has been digested with XhoI and has been ligated with the 1.1 kb XhoI SalI fragment of containing the NEO gene of plasmid pMC1NeoB+ which has been cut with restriction enzyme XhoI and SalI and the small fragment containing the NEO gene has been isolated in substantial accordance with the isolation procedures described above. The resulting plasmid was named W78Neo. Plasmid W78Neo has been further digested with restriction enzyme XhoI and the sticky ends have been filled by DNA polymerase as commonly used by those skilled in the art and as described in the aforementioned Maniatis reference. The blunt ends have been ligated and thus the XhoI site has been destroyed.

Furthermore the above mentioned plasmid W43 has been digested with HindIII and BamHI and the fragment containing exon 3 of the Hprt gene has been isolated. Likewise plasmid pUC19 has been digested with HindIII and BamHI and the isolated fragment has been ligated with the Hprt fragment from plasmid W43. The resulting plasmid was named pRS178.

In the last step of the construction plasmid pRS178 was digested with HindIII and the HindIII fragment of plasmid W78Neo containing the first two exons of the Hprt gene has been ligated with plasmid pRS178. One plasmid having the correct orientation of the two fragments has been named pRS179.

The following description will deal with the construction of the cell line used in one of the preferred embodiments of this specification. Plasmid pRS179 was digested with XhoI to produce a double strand cut within the third exon of the Hprt gene. Digestion was conducted in substantial accordance with the procedure described above.

A celline E14TG2a was used as a host for plasmid pRS179. The celline E14TG2a has been described in an article by Hooper et al. 1987 published in Nature, vol. 326 on pages 292-295 and contains a spontaneous deletion of the first two exons of the Hprt gene described in an article by Hooper et al., published in Nature, vol. 326 on pages 292-295. XhoI digestion of plasmid pRS179 has been used to integrate the plasmid into the Hprt gene in celline E14TG2a and selection was carried out on medium containing hypoxanthine (120 $\mu$M), aminopterine (0.4 $\mu$M) and thymidine (20 $\mu$M), (HAT medium). Other concentrations or combination of concentrations of these agents or other agents are within the scope of this invention as long as they select for a HPRT+ phenotype. Simultanous selection was applied for resistance to G418 resistance (250 $\mu$g per ml). Celline E14TG2a was transformed by electroporation as described in an article by Reid et al., published in Proc. Natl. Acad. Sci. USA, vol. 87 on pages 4299-4303.

Colonies which were able to grow in the presence of HAT medium and G418 were checked for the correct integration of the plasmid pRS179 into the Hprt locus by Southern blotting as described in Example 1. Cellines which contained the correct construct 10 were established.

Reversion of construct 10 to Hprt- allele 22 was selected for on medium containing 6-thiogoanine (6-TG). 6-TG resistant colonies were in the majority of the cases also G418 sensitive. Because the reversion event deletes the integrated plasmid it is henceforth termed deletion (DEL) event.

The constructs of FIGS. 1-5 may be used to detect the presence of chemicals which cause genome rearrangement. The procedure for so using these constructs is described below with regard to the construct of FIGS. 1 to 5. The following section of this specification is a prediction. Based on the fact that the nonmutagenic carcinogens induce the DEL assay with the yeast Saccharomyces cerevisiae, the same assay with mammalian cells will be inducible with the nonmutagenic carcinogens.

It is predicted that at least the most preferred constructs of this invention are substantially more sensitive in detecting carcinogenic chemicals than are prior art short term tests because as described in the allowed patent U.S. Ser. No. 139,345 and as published by Schiestl and Schiestl et al. in the articles entitled "Nonmutagenic carcinogens induce intrachromosomal recombination in yeast." Nature (1998) 337:285-288 and "Carcinogens induce intrachromosomal recombination in yeast." Carcinogenesis (1989) 10:1445-1455 a *Saccharomyces cerevisiae* strain containing a DEL system which is substantially the same structure as construct 10 of FIG. 1 or construct 80 of FIG. 5 is positive with chemicals such as safrole, urethane, ethionine, auramine, methylene chloride, carbon tetrachloride, cadmium chloride, cadmium sulfate, aniline, dimethylhydrazine, aminotriazole, acetamide, thioacetamide, thiourea and 2.2-Bis[4chlorophenyl]-1,1dichloroethylene (DDE), ethylenethiourea and the like.

Although the aforementioned chemicals are all known carcinogens, every one of them tests negative in the widely used prior art "Ames Assay" and other short term tests with yeast. It is particularly remarkable that other in vitro mammalian assays, see e.g. a book by Milman et al. entitled "Handbook of carcinogen testing", Noyes Publications, New Jersey (the publication of which is incorporated by reference into this specification) fail to detect many nonmutagenic carcinogens. The following examples are taken from the aforementioned reference. Thus for example the tests for sister chromatid exchange as well as for chromosome aberrations with mammalian cells are both negative for ethionene, ethylenethiourea and safrole. Thus, for example the syrian hamster embryo clonal transformation procedure is negative with aniline. Thus, for example the rat liver foci assay is negative with safrole and thioacetamide. As mentioned above all of these chemicals are positive with the DEL assay in yeast. Therefore the DEL assay will be inducible with the nonmutagenic carcinogens in mammalian cells.

The process of this invention may be used to screen for any agent which is suspected of causing genome rearrangement. The agent may be in gaseous, liquid, or solid form; it may be an electromagnetic wave; it may be an element or a compound; or it may be some combination thereof.

The suspected agent may be radiation such as, e.g., radiation with a frequency of from $3 \times 10^0$ to $3 \times 10^{22}$. Some of the radiations which are suspected of causing genome rearrangement include, by way of illustration, ultra-violet light, X-rays, gamma-rays, and the like. Often the suspected agent may be a combination of one or more forms of radiation with one or more other agents. Thus, for example, the interaction of X-rays with certain organic matter is believed to often create free radicals which interact with DNA and are believed to cause DNA lesions.

The suspected agent may be any material or form of energy. Some of the agents which the process of this invention can be used to screen are described in a book by H. A. Milman and E. K. Weisburger entitled "Handbook of Carcinogen Testing", (Noyes Publications, Park Ridge, N.J., 1985), the disclosure of which is hereby incorporated by reference into this specification.

In one preferred embodiment, the agent to be tested is one which is not carcinogenic by itself but becomes carcinogenic when metabolized. These agents are often referred to as "procarcinogens" and are described, e.g., on pages 130-149 of said Milman and Weisburger handbook.

When a suspected procarcinogen is to be tested in the process of this invention, one should first provide a medium designed to simulate the metabolism the procarcinogen is subjected to in the body. Thus, for example, for a procarcinogen which can be metabolized in the presence of liver enzymes, one can provide a medium comprised of liver enzymes.

By way of illustration, one can provide a medium containing "S9" (a supernatant of liver homogenate which is described in the aforementioned paper by Ames et al. appearing at pages 347-364 of volume 31, (1975) of *Mutation Research* entitled "Method for Detecting Carcinogens and Mutagens with the Salmonella/Microsome Mutagenicity Test: and which, as is known to those skilled in the art, is commercially available.

In this embodiment, the harvested mammalian cells are incubated in the presence of the suspected carcinogen. In the first step of this process, a viable mouse celline which comprises repeated genetic elements in its haploid genome is provided. The provision of this celline is described in the first portion of this specification.

It is preferred to grow the viable celline in suitable growth medium in order to have a sufficient number of mammalian cells so that the experimental data generated will be statistically significant.

In order to generate a suitable number of the viable mammalian cells, the cells should be grown in a medium which permits growth of the cells which did not undergo genome rearrangement. Those skilled in the art are well aware of suitable media which will permit growth of the cells which did not undergo genome rearrangement. For the meda which can be used and other information about the mammalian cell culture technology see "Animal cell culture: A practical approach" by R. I. Frishney, IRL Press, Washington, D.C. and "Molecular genetics of mammalian cells" in Methods in Enzymology, vol. 151 by M. M. Gottesman, Academic Press, New York, the disclosure of both books is hereby incorporated by reference into this specification.

A suitable medium for permitting growth of the cells which did not undergo genome rearrangement is Dulbecco's Modified Eagle's Medium, supplemented with 15% heatinactivated fetal calf serum and 10 $\mu$M 2-mercaptoethanol. The pluripotent nature of the ES cells was retained by supplementing the growth medium with $10^6$ units per liter of recombinant human Leukemia Inhibitory Factor (LIF), supplied by Dr. N. Gough (Walter and Eliza Hall Institute, Melbourne, Victoria, Australia). Because feeder layers were not used, all cultures were coated with 0.1% sterile gelatine to assure cell adhesion. HAT medium was standard culture medium supplemented with 120 $\mu$M hypoxanthine, 0.4 $\mu$M aminopterine, and 20 $\mu$M thymidine. Culteres were incubated at 37° C. in an atmosphere of 5% $CO_2$. Other suitable growth media can also be used. Thus omissions, and/or additions may be made in the concentrations and/or the compositions of the media described above without adversely affecting their performance and are within the scope of this specification. Some other media used for growth of mammalian cellines can be e.g. found in the aforementioned books by Frishney and Gottesman.

After cells containing the construct of this invention have been grown to a suitably large number, it is preferred to purify the cells so obtained by means well known to those in the art. Thus, for example, one can collect cells by centrifugation or filtration; see, e.g., the books by Frishney and Gottesman. Other suitable separation processes also can be used. Optionally, the mammalian cells may be washed with suitable solution(s).

It is preferred that, after the mammalian cells have been harvested, they are counted in order to determine the number of cells per unit of liquid solution. Conventional means well known to those skilled in the art can be used to count the mammalian cells. Thus, by way of illustration, one can use a hemocytometer (a conventional means of counting red blood cells).

It is preferred to conduct a preliminary experiment to determine those concentrations of the agent to be tested which should be evaluated in the main experiment. Mammalian cells are exposed to or grown in the presence of a wide range of concentrations of the agent to be tested to determine its cytotoxicity.

Suitable concentrations of the agent are used for its evaluation. Several portions of the harvested mammalian cells are used in the experiment. One portion, which is otherwise treated in exactly the same way as the exposed portions, is not exposed to the agent. The other portions of the harvested mammalian cells are exposed to or grown in the presence of the agent at various concentrations. Alternatively, and/or additionally, controlled-variable tests can be conducted with various concentrations of the mammalian cells as well as various concentrations of the agent. As is known to those skilled in the art, the concentration of the mammalian cells might influence the effect of the agent in one or more ways; thus, for example, a dense solution of mammalian cells might shield irradiation more effectively than a dilute solution.

The separated mammalian cells can be exposed to the agent to be tested by various means. In one embodiment, the mammalian cells are mixed with a buffer before such exposure. In another embodiment, the mammalian cells are mixed with a buffer, and the mixture is then diluted directly into the selection medium before being exposed to the agent. In yet another embodiment, the mammalian cells are grown in a growth medium (such as one or more of the media described above which permit the growth of the cells which have not undergone genome rearrangement) in the presence of the agent to be tested. In yet another embodiment, the mammalian cells are grown after exposure to the agent in nonselective medium for variable times before selection is applied.

In the most preferred embodiment it is preferable to grow the cells in a medium which selects against the occurrence of the genome rearrangement to keep the control values as low as possible. In the embodiment described in FIG. 1 it is shown that the NEO gene of construct 10 is lost after the genome rearrangement which results in construct 22. Therefore cells containing construct 10, before the rearrangement are able to grow in the presence of G418 in the medium, but cells containing construct 22, after the genome rearrangement are not able to grow in the presence of G418. After the genome rearrangement cells containing construct 22 are able to grow in the presence of 6-thioguanine in the medium, but cells containing construct 10 before the genome rearrangement are not able to grow in the presence of 6-thioguanine. Therefore the selection scheme which was used for Example 2 involves growth of the mammalian culture in medium in the presence of G418 but without 6-thioguanine before and during the exposure to the potential carcinogens or other test agents. After the exposure the cells which have undergone genome rearrangement are selected on medium in the presence of 6-thioguanine but in the absence of G418.

When the mammalian cells are to be diluted into a suitable selection medium and exposed to the agent, a medium which is both compatible with the agent and which promotes selection for genome rearrangement should be used.

The mammalian cells are then exposed to the agent or agents to be tested. In general, the exposure is conducted under conditions and for a time sufficient to simulate the environment which is being tested for. Thus, e.g., a wide range of reagent concentrations and exposure times is disclosed in said Milman and Weisburger book; they all may be used in the process of this invention under suitable circumstances.

The exposed mammalian cells are characterized by comprising repeated genetic elements in their haploid genomes, which elements are preferably selected from the group consisting of functional and nonfunctional genetic elements. These repeated genetic elements are sufficiently homologous so that, under ambient conditions, they give rise to a genome rearrangement which is identifiable, i.e., when they are present in suitable media they can be distinguished from cells which have not undergone the genome rearrangement. In one preferred embodiment, the genome rearrangement involved with the exposed mammalian cells is a deletion. In another preferred embodiment, the genome rearrangement involved is a duplication. In yet another embodiment, the genome rearrangement involved is a translocation. Regardless of whether the genome rearrangement occurs by deletion or duplication or translocation, the screening procedure described below can be used.

A selection medium is selected for the mammalian celline which, after the mammalian cells have been diluted into it and grown, enables one to identify those mammalian cells which have undergone the specified genome rearrangement. Those skilled in the art are aware of many such growth media which facilitate the identification of such mammalian cells.

Thus, by way of illustration and not limitation, many such media are described in the aforementioned books by Frishney and Gottesman.

As those skilled in the art are aware, each construct requires a certain selection medium which will enable one to identify the cells which have undergone genome rearrangement.

By way of illustration, with the construct of FIG. 1 one can use 6-TG medium for one construct utilizing the Hprt gene as repeated genetic elements. With the constructs of FIG. 2 one can use medium containing hypoxanthine and bromodeoxyuridine and with construct of FIGS. 3 and 4 one can use HAT medium.

As those in the art are aware, some selection media can be used to select for the gain of a function which can arise, e.g., by reversion of a disrupted gene; see, for example, FIGS. 3 and 4. Alternatively, other selection media can be used to select against the presence of one or more genes; see, for example, FIGS. 1, 2 and 5.

After the mammalian cells have been exposed to both the agent to be tested and the selection medium under the conditions of the test and have been incubated for some time period of about more than one day preferably at 37 degrees Celsius or any other temperature which allows growth of the mammalian cells used, the number of colonies formed by cells which have undergone genome rearrangement are counted and compared with the number of colonies of mammalian cells identical in substantially every respect with the exception of not having been exposed to the suspected carcinogenic agent. The rates of genome rearrangement for both the control and experimental samples are then compared.

The experiments should be conducted at different concentrations of the agent to be tested. If the rate of genome rearrangement of the mammalian cells consistently increases with increases in the concentration and/or exposure time of the agent to be tested, then this is one indication that such agent causes genome rearrangement and might be carcinogenic. If, additionally, the rate of genome rearrangement in the presence of one or more concentrations of the agent is substantially greater than the rate in the absence of the agent, this is yet another indication that such agent might be carcinogenic. It should be noted that the rate of increase of genome rearrangement is not necessarily linear with every agent and that some agents might show a lower rate of genome rearrangement with higher concentrations than with lower concentrations. As long as, for at least a certain range of the agent's concentrations, the rate of genome rearrangement is substantially greater than the rate obtained with the control samples, there is some indication that the agent might be carcinogenic.

Several factors influence what will constitute a "substantially greater" rate of genome rearrangement in the process. In the first place, the greater the number of mammalian colonies obtained in the experiment, the lower the difference must be in order to be "substantial". In the second place, if a plot of the rate of genome rearrangement versus concentration of the agent to be tested produces a curve in which, for any two points, the rate of genome rearrangement for the higher concentration of agent is at least equal (and preferably higher than) the rate of rearrangement obtained with the lower concentration the increase might be regarded as substantial. This curve is to be distinguished from a curve obtained in which the rate of genome rearrangement does not consistently increase or at least stay the same as the concentration of the agent is increased. As those skilled in the art are aware, the mammalian cell colonies can be counted by conventional counting means.

The data obtained from the counting of the mammalian cells may be evaluated by means well known to those skilled in the art. Thus, for example, one may use procedures described in an a book by Milman and Weisburger entitled "Handbook of carcinogen testing" Noyes Publications, New Jersey.

The most preferred embodiments within the scope of this invention is predicted to have the advantage that the basis frequency obtained with the control shows better reproducibility than the control values obtained with other recombination systems in mammalian. This is because the preferred medium used for precultivation of the cells selects against the genome rearrangement so that only the spontaneous frequency, which is in this case similar to the rate, is obtained. Thus the effect known as "Jack pot" to those skilled in the art is avoided.

EXAMPLES

The following examples are presented to illustrate the claimed invention but are not to be deemed limitative thereof. Unless otherwise specified, all parts are by weight and all temperatures are in degrees centigrade.

Example 1 relate to one preferred embodiment of this invention, which is illustrated in FIG. 1 as construct 10 and whose construction is described in detail in the specification. Example 1 describes the construction of construct 10 in further detail. Construct 80 of FIG. 5 has been constructed and published previously and the construction thereof is therefore not incorporated in this specification in detail. Many of the procedures for constructing and/or characterizing construct 10 are well known to those skilled in the art. These prior art procedures are illustrated in the Examples by reference to prior art publications, each of which is hereby incorporated into this specification.

EXAMPLE 1

Construction of the recombination system

A mammalian celline which comprises construct 10 of FIG. 1 is provided. The particular celline used by the applicant was E14TG2a which had a spontanous deletion of the first two exons of the Hprt gene isolated and published in an article by Hooper et al. 1987 in Nature 326 on pages 292-295.

The media for growth of mammalian cells are well known to those skilled in the art and have been described in an earlier part of this specification.

pRS179 was constructed as follows: In the process of producing one of the preferred embodiments used in the invention, plasmid pDWM101 (published in an article by Thompson et al. 1989 in Cell, vol. 56 on pages 313-321) has been cut at the restriction sites for the endonuclease HindIII and both fragments subcloned. The resulting fragments have been isolated. The procedure for digesting plasmids with restriction enzymes and of isolating the fragments so digested is well known to those skilled in the art. Thus, by way of illustration and not limitation, one may refer to a publication by T. Maniatis et al. entitled "Molecular Cloning: A Laboratory Manual", (Cold Spring Harbor Laboratory, Cold Spring Harbor, N.Y., 1982). In the Maniatis Laboratory Manual, restriction enzymes are disclosed on pages 97-107, and the isolation of gene fragments by Gel Electrophoresis is described on pages 149-186. The Maniatis Laboratory Manual is hereby incorporated by reference in its entirety into this specification.

Plasmid DWM101 was digested with the restriction endonuclease HindIII, for definition and properties of restriction enzymes see an earlier part of this specification, restriction enzymes were purchased from Bethesda Research Laboratory of Gaithersburg, Md.) and the two fragments were separated by agarose gel electrophoresis in a commercially available gel tank obtained from Bethesda Research Laboratories of Gaithersburg, Md. A gel was prepared with 0.7% agarose (ultra pure, from Sigma Chemical Company of St. Louis, Mo. 63178) in TBE buffer containing per liter of distilled water 10.8 gram Tris (hydroxymethyl) aminomethane (hereinafter called Tris-base), 5.5 gram boric acid and 0.93 gram disodium ethylene diamine tetraacetate dihydrate (hereinafter called EDTA). The agarose was boiled in TBE buffer until dissolved and after cooling to 45° C. poured into the gel tank. The solidified gel was submerged into TBE buffer and the gel was electrophoresed with a commercially available power supply (from Bethesda Research Laboratories) at 30 volts for 12 hours. The DNA was made visible under UV light by staining with 0.5 microgram per milliliter ($\mu$g/ml) ethidium bromide and the desired band was located. The DNA fragment was isolated according to a publication by Dretzten et al. entitled "A reliable method for the recovery of DNA fragments from agarose and acrylamide gels" as appeared in Analytical Biochemistry 112 on pages 295 to 298 (1981). An incision was made with a scalpel in front of the band and a piece of Wattman DE81 DEAE-cellulose paper (obtained from Fisher Scientific of Pittsburgh, Pa.) was inserted. The band was allowed to enter the DEAE paper by further electrophoresis in the same direction and thereafter the paper was removed from the gel. The paper was placed into a 0.4 ml Eppendorff tube and a hole was made in the bottom of the tube, the tube was placed inside a 1.5 ml Eppendorff tube and spun for 15 seconds in a Fisher microfuge, 0.1 ml of elution buffer containing 0.2 molar sodium chloride, 50 millimolar Tris base with a pH of 7.6, one millimolar EDTA and 0.1% of sodium dodecyl sulfate (obtained from Sigma Chemical Corporation) was added and the elution buffer collected by centrifugation. This was repeated twice and the eluate was extracted once with an equal volume of phenol, once with a 1:1 mix of phenol chloroform and once with chloroform. The obtained solution was precipitated with twice the volume of ice cold ethanol for 30 minutes at −20° C. Thereafter the precipitate was washed with a 70% solution of ethanol, vacuum dried, and redissolved in 10 ml of double distilled water.

The isolated fragments from plasmid pWM101 were ligated with DNA ligase purchased from the Bethesda Research Laboratory, of Gaithersburg, Md. The fragment containing the vector was ligated onto itself and the resulting plasmid was named W43, the fragment without a vector was ligated with pUC8 after digestion with HindIII and named W78. Ligation was carried out by adding 0.2 Weiss units of T4 DNA ligase (obtained from Boehringer Mannheim, Indianapolis, Ind.) and one tenth of the following ligation buffer: 0.5 molar Tris base with a pH of 7.4, 0.1 molar magnesium chloride, 0.1 molar dithiothreitol, 10 millimolar spermidine, 10 millimolar adenosine triphosphate, and one milligram per milliliter of bovine serum albumine. Ligation was performed over night at 4° C.

E. coli strain SF8 was transformed with the ligation mix. E. coli transformation was started with an overnight culture of strain SF8 in LB medium. It is believed that strain SF8 has the following genotype: hsdr-, hsdm- , recA1, supE44, lacz4, leuB6, proA2, and thi1. 5 ml of Luria Broth (LB) medium containing 10 grams of tryptone, 5 grams of yeast extract, (both ingredients obtained from Difco Laboratories of Detroit, Mich.) 5 grams of sodium chloride per liter of medium was inoculated with a single bacterial colony, incubated overnight at 37° C. in a New Brunswick incubator with vigorous shaking. 0.3 ml of this culture were inoculated into 30 ml of fresh LB medium and incubated under vigorous shaking at 37° C. until the culture reached an OD at 600 nanometers of 0.6. The culture was chilled by placing onto an ice water bath and thereafter the cells were collected by centrifugation at 6,000 rounds per minute (hereinafter called rpm) in a Sorvall centrifuge for five minutes. In the ice water bath one milliliter of an ice cold solution of 50 millimolar calcium chloride was added to the cell pellet and mixed. Ten microliter of the ligation mix was added to 5 μl of a solution of one molar calcium chloride and 85 μl of buffer containing 10 millimolar of the aforementioned Tris-base and one millimolar EDTA adjusted to pH 8.0 with hydrochloric acid (this buffer is hereinafter called Tris/EDTA pH 8.0). 0.2 milliliter of cell suspension was added to the DNA solution in small cooled plastic tubes. The solution was mixed gently and left on ice for 30 minutes. Thereafter the suspension was heated to 45° C. in a water bath for two minutes and then placed again into the ice bath to cool down. Three milliliter of LB medium was added and the tubes were incubated at 37° C. for two hours. Thereafter the cells were collected by centrifugation at 6.000 rpm for 5 minutes and the cell pellet suspended in 0.5 ml LB medium. 0.1 milliliter were plated onto each of LB plates containing 100 micrograms (hereinafter abbreviated μg) per milliliter of Ampicillin (obtained from Sigma Chemical Company).

Ampicillin resistant colonies were isolated and plasmid DNA was isolated from them as a modification of the boiling method, published by Holmes and Quigley in a publication entitled "A rapid boiling method for the preparation of bacterial plasmids." Anal. Biochem. 114:193-197 (1981). One milliliter of *E coli* culture containing the plasmid of interest was grown overnight in LB medium containing ampicillin. The cells were transferred to a 1.5 ml Eppendorff tube and spun down in a microfuge. The cells were resuspended in 0.4 ml of STET buffer consisting of 1 molar Tris-base adjusted to pH 7.5 with hydrochloric acid, 20% triton (purchased from Sigma Chemical Company), 50% sucrose and 0.5 molar EDTA. Further 40 μl of a solution containing 10 mg of lysozyme (purchased from the aforementioned Sigma Chemical Company) per milliliter of double glass distilled water was added and the solution mixed. The solution was further boiled for 50-60 seconds and immediately thereafter placed in an ice-waterbath for 1 minute. The solution was spun in a microfuge for 10 minutes at four degrees Celsius and thereafter the resulting pellet was removed with a sterile toothpick. Further 500 milliliter of cold (−20 degrees Celsius) isopropanol was added the content mixed by inverting the tube several times and the tube was thereafter left in the freezer (−20 degrees Celsius) for 10 minutes. The solution was furthermore spun for 3 minutes in the microfuge at four degrees Celsius and afterwards the supernatant discarded; the pellet was resuspended in 50 μl of a Tris/EDTA buffer adjusted to pH 8.0 with hydrochloric acid and 50 μl of a solution consisting of 5 molar lithiumchloride and 50 millimolar Tris/EDTA pH 8.0 was added. The content of the tube was furthermore mixed and incubated in an ice-waterbath for 5 minutes. Thereafter the content was spun in a microfuge for 5 minutes at 4 degrees Celsius and the supernatant was removed and placed into a new Eppendorff tube. Furthermore 200 μl of cold Ethanol (−20 degrees Celsius) was added and after mixing of the content by inverting the tube several times the tube was left at −20 degrees Celsius for 10 minutes. After spinning of the tube for 3 minutes at 4 degrees Celsius the precipitate was washed with one half milliliter of 80% ethanol. After another spin for 3 minutes in the microfuge at 4 degrees Celsius the precipitate was dried in an Exsiccator by means of creating a vacuum with a waterpump for several minutes until the precipitate was dry. Thereafter the precipitate was dissolved in 60 μl of double glass distilled water of Tris/EDTA pH 8.0 depending on the further procedure. The resulting solution contained about 2 microgram of plasmid DNA which was cut with restriction enzymes to determine which of the colonies contained the correct construct.

Plasmid W78 was digested with EcoRI upstream of the first exon of the Hprt gene. Using XhoI linkers a XhoI site has been introduced flanked by EcoRI site. The creation of new restriction sites with linkers is well known to those skilled in the art. Thus, by way of illustration and not limitation, one may refer to the above cited publication by T. Maniatis et al. entitled "Molecular Cloning: A Laboratory Manual", (Cold Spring Harbor Laboratory, Cold Spring Harbor, N.Y., 1982). The resulting plasmid has been digested with XhoI and has been ligated with the 1.1 kb XhoI SalI fragment of containing the NEO gene of plasmid pMC1NeoB+ which has been cut with restriction enzyme XhoI and SalI and the small fragment containing the NEO gene has been isolated in substantial accordance with the isolation procedures described above. The resulting plasmid was named W78Neo. Plasmid W78Neo has been further digested with restriction enzyme XhoI and the sticky ends have been filled by DNA polymerase as commonly used by those skilled in the art and as described in the aforementioned Maniatis reference. The blunt ends have been ligated and thus the XhoI site has been destroyed.

Furthermore the above mentioned plasmid W43 has been digested with HindIII and BamHI and the fragment containing exon 3 of the Hprt gene has been isolated. Likewise plasmid pUC19 has been digested with HindIII and BamHI and the isolated fragment has been ligated with the Hprt fragment from plasmid W43. The resulting plasmid was named pRS178.

In the last step of the construction plasmid pRS178 was digested with HindIII and the HindIII fragment of plasmid W78Neo containing the first two exons of the Hprt gene has been ligated with plasmid pRS178. One plasmid having the correct orientation of the two fragments has been named pRS179.

Plasmid pRS179 was isolated large scale from *E. coli*:5 milliliter of LB medium with ampicillin was inoculated with a single bacterial colony, incubated overnight at 37° C. in a New Brunswick incubator with vigorous shaking. 2.5 milliliter of the overnight culture was inoculated into a two liter flask containing 500 milliliter of M9aa minimal medium: M9aa medium contained per liter of distilled water solution, 6 gram of sodium phosphate ($Na_2HPO_4$), 3 gram of potassium phosphate ($KH_2PO_4$) 0.5 gram of sodium chloride (NaCl), one gram of ammonium chloride ($NH_4Cl$) and 4 gram casaminoacids (obtained from Difco Laboratories). The medium was adjusted to a pH of 7.4, sterilized by autoclaving and after cooling the following solutions were sterilized by filtration and added, two milliliter of one molar magnesium sulphate (MgSO$_4$), 10 milliliter of 20% w/v glucose, 100 µl one molar calcium chloride (CaCl$_2$) and one milliliter of 100 µg/ml of Ampicillin. The culture was vigorously shaken at 37° C. until it reached an OD at 600 nanometer of 0.6 and 65 milligram of chloramphenicol (purchased from Sigma Chemical Comp.) were added and the culture was further incubated for another 14 hours in the same way. The cells were separated by centrifugation in a GSA rotor for 10 minutes at 5000 rpm in a Sorvall centrifuge. Thereafter the cells from one liter initial culture were resuspended in 100 ml TS buffer containing 10% sucrose and 0.05 mol Tris-base adjusted to pH 8.0 with hydrochloric acid. The cell were again collected by centrifugation as described above and were chilled at 0° C. in an ice-water bath and resuspended in 10 ml ice cold TS buffer and transfered to a 50 ml flask. Two milliliter of a solution of 5 mg/ml of freshly dissolved lysozyme (obtained from Sigma Chemical Comp.) was added and the solution was mixed gently on ice for 10 minutes, four milliliter of a solution of ice cold 0.25 molar EDTA was added gently from the bottom of the flask and the mix left on ice for five minutes. 15 milliliter of triton lysis buffer consisting of a solution in distilled water of 10% triton X-100, 0.05 molar Tris base adjusted to a pH of 8.0 with hydrochloric acid, 0.05 molar EDTA were added and the solution was left for 10 minutes on ice. Thereafter the solution was spun in a SS34 rotor in a Sorvall centrifuge with 18,000 rpm at 4° C. for 60 minutes. The supernatant was collected and an equal volume of phenol, equilibrated with TE buffer, consisting of a solution in distilled water of 10 millimolar Tris base adjusted to a pH of 8.0 with hydrochloric acid and 1 millimolar EDTA, and an equal amount of chloroform was added. The solution was shaken for 3 minutes at room temperature and thereafter spun at 5.000 rpm in a SS34 rotor in a Sorvall centrifuge for 10 minutes and the supernatent was collected. The same procedure starting with the addition of phenol was repeated a second time and the water phases were joined and 17.5 milligram of sodium chloride was added per milliliter of solution. Absolute ethanol was added at twice the volume of the solution, the solution was gently mixed and left for 30 minutes in a freezer at −20° C. The solution was spun at 5.000 rpm for 5 minutes and thereafter the pellet containing the DNA was washed with 80% in distilled water of ethanol. The pellet was dried in an exsiccator and was then dissolved in 5 ml TE buffer.

Another purification step using cesium chloride gradient centrifugation was added. To the TE solution 0.75 milliliter of a buffer consisting of one molar Tris base adjusted to a pH of 7.5 with hydrochloric acid and 0.1 milliliter of 0.5 molar EDTA in distilled water was added. 0.978 gram of cesium chloride per (weight of solution in gram plus 1.2) was added and the volume split in half and added each into a nitrocellulose centrifuge tube of a 50 Ti rotor, and 0.6 milliliter of 5 mg/ml of ethidium bromide was added to each and the solution topped up with paraffin, and the tubes were sealed. The tubes were mixed well and spun in a Beckman ultracentrifuge for 40 hours at 40.000 rpm at 20° C. The plasmid band was located using UV light and was removed with a syringe and transfered to a 30 ml centrifuge tube. The ethidium bromide was extracted five times with an equal volume of butan-1-ol which was saturated with TE buffer. The DNA was precipitated with three volumes of 70% ethanol in distilled water at −20° C. for one hour and collected by centrifugation at 10.000 rpm for 15 minutes in a SS34 rotor in a Sorvall centrifuge and dissolved in 0.5 ml TE buffer. The DNA solution was dialysed against TE buffer for 20 hours with changes of the buffer. The OD at 260 nanometer of the solution was determined and the concentration of DNA calculated. The yield was about 700 µg of plasmid DNA.

The following description will deal with the construction of the cell line used in one of the preferred embodiments of this specification. Plasmid pRS179 was digested with XhoI to produce a double strand cut within the third exon of the Hprt gene. Digestion was conducted in substantial accordance with the procedure described above.

A celline E14TG2a was used as a host for plasmid pRS179. The celline E14TG2a has been described in an article by Hooper et al. 1987 published in Nature, vol. 326 on pages 292–295 and contains a spontaneous deletion of the first two exons of the Hprt gene described in an article by Hooper et al., published in Nature, vol. 326 on pages 292–295. XhoI digestion of plasmid pRS179 has been used to integrate the plasmid into the Hprt gene in celline E14TG2a and selection was carried out on medium containing hypoxanthine (120 µM), aminopterine (0.4 µM) and thymidine (20 µM), (HAT medium). Other concentrations or combination of concentrations of these agents or other agents are within the scope of this invention as long as they select for a HPRT+ phenotype. Simultaneous selection was applied for resistance to G418 resistance (250 µg per ml). Celline E14TG2a was transformed by electroporation as described in an article by Reid et al., published in Proc. Natl. Acad. Sci. USA, vol. 87 on pages 4299–4303.

Colonies which were able to grow in the presence of HAT medium and G418 were checked for the correct integration of the plasmid pRS179 into the Hprt locus by Southern blotting as described in Example 1. Cellines which contained the correct construct 10 were established.

Reversion of construct 10 to Hprt allele 22 was selected for on medium containing 6-thiogoanine (6-TG). 6-TG resistant colonies were in the majority of the cases also G418 sensitive. Because the reversion event deletes the integrated plasmid it is henceforth termed deletion (DEL) event.

I claim:

1. A process for screening an agent to determine its effect upon the frequency of deletions in mammalian cells, comprising the steps of:
   (a) exposing the agent to be tested to a viable mammalian cell line which comprises repeated genetic elements in its haploid genome, wherein:
      1. said repeated genetic elements are selected from the group consisting of functional and non-functional genetic elements, and
      2. said repeated genetic elements are sufficiently homologous so that, under ambient conditions, they recombine with each other and give rise to an identifiable deletion at a rate of at least about $1 \times 10^{-11}$ occurrences per cell per generation;
   (b) contacting said exposed viable mammalian cell line with a growth medium which; after growth of mammalian cells, enables the identification of those mammalian cells which have undergone said deletion;

(c) incubating said exposed viable mammalian cell line while it is in contact with said growth medium; and (d) determining the extent to which exposed mammalian cells in said exposed mammalian cell line have undergone said deletion.

2. The process as recited in claim 1, wherein at least one of said repeated genetic elements is a deletion allele.

3. The process as recited in claim 1, wherein said genetic elements are deletion alleles which give rise to a functional allele which is selectable after said deletion.

4. The process as recited in claim 3, wherein said mammalian cell line prepared by disrupting a gene which is selectable.

5. The process as recited in claim 3, wherein said repeated genetic elements flank a gene which is selectable.

6. The process as recited in claim 5, wherein said genetic elements are selected from the group consisting of HPRT, TK, NEO, HPH (HYG), and XGPT.

7. The process as recited in claim 5, wherein said gene which is selectable is selected from the group consisting of HPRT, TK, NEO, HPH (HYG), and XGPT.

8. The process as recited in claim 7, wherein said genetic elements are fragments of the HPRT gene.

9. The process as recited in claim 8, wherein said gene which is selectable is the NEO gene.

10. The process as recited in claim 1, wherein one of said repeated genetic elements is a functional allele.

11. The process as recited in claim 10, wherein one of said repeated genetic elements is a wild type allele which is selectable.

12. The process as recited in claim 11, wherein said wild type allele is selected from the group consisting of HPRT and TK.

13. The process as recited in claim 12, wherein said genetic elements have been constructed by correcting a deletion.

14. The process as recited in claim 1, wherein said genetic elements flank a gene which is selectable.

15. The process as recited in claim 14, wherein said gene which is flanked by the genetic elements is selected from the group consisting of TK and HPRT.

16. The process as recited in claim 2, wherein said genetic elements reside on different chromosomes.

17. The process as recited in claim 2, wherein said mammalian cells are prepared by integration of a plasmid into their genome.

18. The process as recited in claim 17, wherein said plasmid contains a fragment of a gene which upon integration into the genome, provides said genetic elements.

19. The process as recited in claim 18, wherein said plasmid contains a fragment of the HPRT gene.

* * * * *